United States Patent [19]
Lamparski et al.

[11] Patent Number: 5,783,435
[45] Date of Patent: Jul. 21, 1998

[54] PROSTATE CANCER DRUG SCREENINGS

[76] Inventors: Henry G. Lamparski, 422 S. El Dorado, San Mateo, Calif. 94402; Eric R. Schuur, 20350 Stevens Creek Blvd., #305, Cupertino, Calif. 95014; Daniel R. Henderson, 995 Matadero Ave., Palo Alto, Calif. 94306

[21] Appl. No.: 692,759

[22] Filed: Aug. 6, 1996

[51] Int. Cl.$^6$ ............................ C12H 1/20; G01H 33/53; C07H 21/04

[52] U.S. Cl. ...................... 435/252.3; 435/7.1; 435/7.23; 435/320.1; 435/326; 536/24.1

[58] Field of Search ................................. 435/7.1, 7.23, 435/252.3, 320.1, 326; 536/24.1

[56] References Cited

FOREIGN PATENT DOCUMENTS

| 96/14875 | 5/1996 | WIPO. |
|---|---|---|
| WO 96/14875 | 5/1996 | WIPO. |

OTHER PUBLICATIONS

Culig, Z. et al. 1994. Cancer Research, 54: 5474–5478.
Pang, S. et al 1995. Human Gene Therapy, 6: 1417–1426.
Decensi, A. et al. 1994. The Prostate, 24: 17–23.

de Wet et al., "Firefly luciferase gene: structure and expression in mammalian cells" Molecular and Cellular Biology (1987) 7(2):725–737.

Pang et al., "Prostate tissue specificity of the prostate-specific antigen promoter isolated from a patient with prostate cancer" Human Gene Therapy (1995) 6:1417–1426.

Schuur et al., "Prostate-specific antigen expression is regulated by an upstream enhancer" Journal of Biological Chemistry (1996) 271(12):7043–7051.

*Primary Examiner*—Lila Feisee
*Assistant Examiner*—Minh-Tam Davis

[57] ABSTRACT

Screening of compounds for activity toward inhibition of prostate cancer cell proliferation is provided. A cell line is employed which can be used in conventional equipment for determining activity of compounds, where the cell line uses a marker whose expression is responsive to therapeutically active compounds.

13 Claims, 1 Drawing Sheet

PROSTATE CANCER DRUG SCREENINGS

BACKGROUND

Prostate cancer is the fastest growing neoplasm in men with an estimated 244,000 new cases in the United States being diagnosed in 1995, of which approximately 44,000 deaths will result. Hormonal ablation therapy, either surgically or chemically with anti-androgens, is the main stay of treatment for advanced carcinoma of the prostate. However, androgen ablation therapy failed within 12-18 months with the disease becoming androgen independent. Following the failure of androgen therapy, the median patient survival time is eight months. Other approaches to treating prostate cancer—external radiation, radioactive seed therapy, cryotherapy, etc.—are directed toward organ confined disease of the prostate and are unable to treat metastatic tumors.

The prostate-specific antigen (PSA), a member of the human kallikrein gene family, is a Mr=34,000 chymotrypsin like protein that is synthesized exclusively by normal, hyperplastic, and malignant prostatic epithelia. Hence, the PSA's tissue-specific relationship has made it an excellent biomarker for identifying benign prostatic hyperplasia (BPH) and prostatic carcinoma (CaP), hereinafter CaP. Normal serum levels of PSA and blood are typically below 5 ng/ml, with elevated levels indicative of BPH or CaP. Serum levels of 200 ng/ml have been measured in end-stage metastatic CaP.

In the last few years, numerous techniques have been developed for producing vast arrays of potential drug-like compounds. These compounds not only include oligomers, such as oligopeptides and oligonucleotides, but also synthetic organic compounds based on various core structures. In addition, various natural sources have been screened for active compounds, such as those found in jungles, the ocean, and the like. Thus, there is a great proliferation of available compounds for screening for physiological activity.

The process of identifying prospective compounds having therapeutic activity is primarily held back by the absence of useful screening assays. In order for a screening assay to be useful, it should be capable of automation, allow for the screening of large numbers of samples without requiring extensive equipment or housing, be relatively inexpensive, and provide for a clear indication of activity. There is, therefore, substantial interest in identifying new screening assays which would allow for the screening of compounds which may have therapeutic activity in relation to prostate cancer.

SUMMARY OF THE INVENTION

Methods and compositions are provided for screening therapeutic agents for the treatment of prostate cancer. The methods employ a PSA expressing stably transformed epithelial cell line comprising a construct of the PSA gene enhancer/promoter and a marker gene, e.g. luciferase. The cells are shown to be responsive to the addition of androgen agonists and antagonists by the modified expression of the marker gene.

DESCRIPTION OF THE SPECIFIC EMBODIMENTS

Figure 1A:
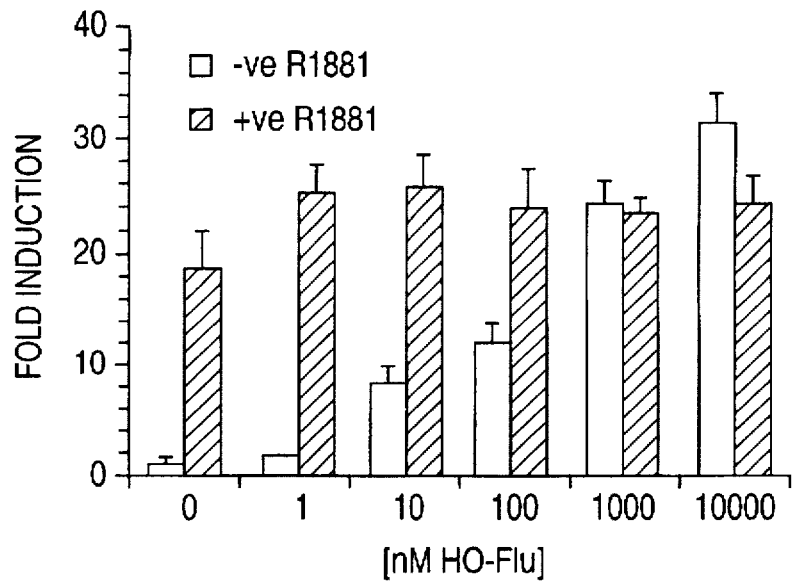
FIG. 1 is a bar graph of antiandrogen induction/inhibition on luciferase expression by the cell line CN1013, FIG. 1A indicating induction by hydroxyflutamide, and FIG. 1B by cyproterone acetate, before (white bars) and after (dark bars) induction with 1 nM R1881.

Methods are provided for screening compounds for therapeutic effect against prostate cancer. The method comprises adding the compound in an appropriate medium to PSA producing cells into which has been stably introduced a genetic construct comprising the enhancer/promoter of the prostate-specific antigen (PSA) with a structural gene under the transcriptional regulation of the PSA enhancer/promoter, which structural gene provides for a detectable, quantifiable signal. By measuring the effect of the candidate compound on the level of signal observed as compared to a basal level, one can evaluate the potential of the compound as a therapeutic agent for the treatment of prostate cancer. Particularly, anti-androgenic activity can be evaluated as indicative of therapeutic effects for prostate cancer.

The cells which are employed in the screening are stable prostate cancer cell lines which express PSA, particularly based on the LNCaP cell line, which are cells derived from a metastatic tumor isolated from a lymph node. This cell line has been established for an extended period of time, stably maintains expression of PSA, and is readily grown in conventional media.

The subject cells are produced by introducing an expression construct into a stable prostate cancer cell line expressing PSA at at least a level of 10 to 20 ng/mL per $10^6$ cells per day. The expression construct comprises as the transcriptional initiation regulatory region, the PSA enhancer with the PSA promoter or a different promoter region, usually the PSA promoter. The 5'-non-coding region of the PSA gene may include the region from 0 (the site of transcription initiation) to −6000 or may be truncated, to provide only those sequences essential for the enhancer region and the promoter region. Thus, the particular regions include the enhancer active sequences between −5824 and −3738 with the promoter active region, for the PSA gene, the region from about −560 to +7.

This transcription initiation regulatory region may then be joined to a marker gene which provides for a detectable, desirably quantifiable, signal. Of particular interest are genes which provide for luminescence, such as luciferase, aequorian, β-galactosidase, chloramphenicol, etc. In addition, one may provide for a marker for selection comprising a constitutive transcriptional initiation region and an antibiotic resistance gene, e.g. neo. In this way, one may select for those cells which have the expression construct stably integrated.

The construct may be prepared in accordance with conventional ways, introducing each of the components of the construct into a plasmid by employing convenient restriction sites, PCR to introduce specific sequences at the termini, which may include providing for restriction sites, and the like. After the expression construct has been prepared, it may be introduced into the cells by any convenient means.

Methods for introducing the expression construct into the cell line include transfection, complexing with cationic compounds, lipofection, electroporation, and the like. The cells may be expanded and then screened for the presence of the expression construct. Where an antibiotic resistance gene has been introduced, the cells may be selected for antibiotic resistance and the antibiotic resistance cells then screened for luminescence under appropriate conditions. In the absence of the antibiotic resistance, the cells may be directly screened for luminescence. Conveniently, the assay for luminescence is performed on a lysate using conventional reagents.

After selecting clones which demonstrate high levels of luciferase activity when activated, the induction ratio may be further enhanced by performing limiting dilution with the cells and screening the resulting clones. In this manner, the induction may be at least 20 fold when induced with 0.1–1 nM R1881, preferably at least about 50 fold, and more preferably at least about 100 fold. Usually, the induction will not exceed about 500 fold.

The cells are desirably grown in hormone-free medium, e.g. RPMI medium supplemented with 10% fetal bovine serum, 100 units/ml penicillin and 100 µg/ml streptomycin, and assayed in hormone spiked medium, e.g. 10% strip-serum RPMI with hormone. Desirably, the cells should not have been passaged more than about 50 times, more desirably not more than about 25 times.

The luminescence may be determined in accordance with conventional commercial kits, e.g. enhanced luciferase assay kit (Analytical Luminescence Laboratory, MI). The cells may be distributed in multiwell plates which can be accommodated by a luminometer. A known number of cells is introduced into each one of the wells in an appropriate medium, the candidate compound added, and the culture maintained for at least 12 hours, more usually at least about 24, and not more than about 60 hours, particularly about 48 hours. The culture is then lysed in an appropriate buffer, using a non-ionic detergent, e.g. 1% triton X-100. The cells are then promptly analyzed, usually within about 30 minutes, preferably in from about 10–15 minutes, or may be stored frozen (–80° C.) until thawed, and then promptly assayed. In conjunction with the candidate compound, an inducing compound, e.g. androgens, will also be added such as methyl trienolone (R1881), or dihydrotestosterone (DHT). The concentration of these agonists will vary depending upon the nature of the agonist, but will be sufficient to induce expression. The concentration with R1881 will generally be in the range of about 0.1–10 nM, preferably about 1 nM.

Any other technique for detecting the level of luminescence may be used. The particular manner of measuring luminescence is not critical to the invention.

The following examples are offered by way of illustration and not by way of limitation.

EXPERIMENTAL

Materials and Methods

Cells and Culture Methods. LNCaP cells were obtained at passage 9 from the American Type Culture Collection (Rockville, Md.). LNCaP cells were maintained in RPMI 1640 medium (RPMI) supplemented with 10% fetal bovine serum (FBS; Intergen Corp.), 100 units/mL of penicillin, and 100 units/mL streptomycin. LNCaP cells being assayed for luciferase expression were maintained in 10% strip-serum (charcoal/dextran treated fetal bovine serum to remove T3, T4, and steroids; Gemini Bioproduct, Inc., Calabasas, Calif.) RPMI. The cells were periodically tested for the production of PSA which was consistently above 20 ng/mL per day.

Selection for a stably integrated plasmid DNA was performed in RPMI medium containing G418 (GibcoBRL, N.Y.). The level of G418 in RPMI was decreased from 500 to 100 µg/mL after selection of the parental LNCaP clones for evaluation; these clones were maintained in 100 µg/mL G418 at all times prior to assaying. Subclones having enhanced luciferase activity were obtained from the parental cell line by the method of limited dilution cloning.

PSE-Luciferase (CN1) Plasmid Constructs. The luciferase gene from Photinus Pyralis from the plasmid pJD206 (de Wet et al., Molecular and Cellular Biology (1987) 7:725–737) was excised by cleavage with restriction enzymes HindIII and BamHI, then ligated into similarly cleaved pUC18. This plasmid was then cleaved with HindIII and KpnI again to remove the luciferase fragment which was then ligated into similarly cleaved pBluescript KSII(+) (Stratagene). The resulting plasmid was designated LB78. The 5.8 kb HindIII fragment containing the PSA gene upstream region was excised from the plasmid CN0 (Schuur et al., J. Biol. Chem. (1996) 271:7043–7051) and ligated to HindIII-cleaved LB78. A clone was selected with the cap site of the PSA gene in the PSA gene fragment adjacent to the beginning of the luciferase gene to drive its synthesis. The resulting clone was designated CN1 (PSE-Luc).

Transfections of LNCaP Cells. For transfections, LNCaP cells were plated out at a cell density of $5 \times 10^5$ cells per 6-cm culture dish (Falcon, N.J.) in complete RPMI. DNAs were introduced into LNCaP cells after being complexed with a 1/1 molar lipid mixture of N-[1-(2,3-dioleyloxy)propyl-N, N,N-trimetylammonium chloride (DOTAP; Avanti Polar Lipids, AL) and dioleoyl-phosphatidylethanolamine (DOPE; Avanti Polar Lipids, AL); DNA/lipid complexes were prepared in serum-free RPMI at a 2/1 molar ratio. Typically, 8 µg (24.2 nmole) of DNA was diluted into 200 µL of incomplete RPMI and added dropwise to 50 nmole of transfecting lipids in 200 µL of RPMI with gentle vortexing to insure homogenous mixing of components. The DNA/lipid complexes were allowed to anneal at room temperature for 15 minutes prior to their addition to LNCaP cells. Medium was removed from LNCaP cells and replaced with 1 mL of serum-free RPMI followed by the dropwise addition of DNA/lipid complexes. Cells were incubated with complexes for 4–5 hours at 37° C., 5% $CO_2$. Medium was removed and cells washed once with PBS. The cells were then trypsinized and resuspended in 10% strip-serum RPMI (phenol red free). Cells were replated into an opaque 96-well tissue culture plate (Falcon, N.J.) at a cell density of 40,000 cells/well per 100 µL media and assayed. Varying amounts of drugs (e.g. androgens and antiandrogens) were added 16 hours later and assayed for luciferase activity 32 hours thereafter.

Generation of a stably transfected cell line expressing luciferase was accomplished by co-transfecting the plasmid pcDNA3 with PSE-Luc. The neomycin gene of pcDNA3 confers resistance to the antibiotic G418, allowing selection of stably transfected LNCaP cells. LNCaP cells were co-transfected with PSE-Luc and pcDNA3 as described for transient transfections. Briefly, 1 µg of pcDNA3 and 1–10 µg of PSE-Luc were diluted into 200 µL of RPMI and complexed with two molar equivalents of DOTAP/DOPE (1:1) in 200 µL RPMI. Addition of DNA to lipids was dropwise with gentle vortexing to homogeneously mix the samples. After annealing the complexes for 15 minutes, they were added dropwise to LNCaP cells in 1 mL RPMI and incubated overnight (12 hours) at 37° C. Media/DNA-lipid complexes were removed from the tissue culture plates and supplemented with complete RPMI containing 500 µg/mL G418. The selection media was kept at 500 µg/mL G418 for three weeks before being lowered to 250 µg/mL. G418 resistant colonies appeared after four weeks and were allowed to grow until visible by eye, upon which colonies were trypsinized (0.25% trypsin) and transferred to a 24 well tissue culture plate, followed by further expansion. Clones were assayed for luciferase expression after they had reached $3–5 \times 10^6$ cells. Screening identified the clone CN1013 which was selected for further study. A clone 5–10 fold more active than CN1013, designated CN1013.7, was obtained by subcloning the parental line once by limiting dilution.

Induction and Assaying of Transient and Stable PSE-Luc/LNCaP Cells. For both transient and stably transfected LNCaP cells, a variety of androgens and antiandrogens—methyl trienolone (R1881, DuPont NEN), dihydrotestosterone (DHT, Sigma), cyproterone acetate (CA and hydroxyflutamide (Ho-Flu)—were used to induce expression of the luciferase reporter gene. Androgens or antiandrogens were prepared at 3× concentrations in 10% strip-serum RPMI and added as 50 µL aliquots to each well of the 96-well plate. Cells were incubated with either androgens or antiandrogens for 48 hours before assaying. Assays were done in triplicate or quadruplicate. The concentration of dihydrotestosterone (DHT) was measured by the Testosterone ELISA Kit (Neogen Corporation). The assay has 100% cross reactivity with DHT.

In the case of stably transfected PSE-Luc/LNCaP clones, media was removed and cells washed with PBS (2×20 mL). The clonal cells were then maintained in 10% strip-serum RPMI (phenol red free) for 24 hours prior to trypsinizing and replating into an opaque 96-well plate—40,000 cells/well per 100 µL media. Cells were allowed to become adherent overnight before the addition of either androgens or antiandrogens. Incubation of clonal cells in strip-serum RPMI prior to induction with drug(s) substantially lowered background luciferase expression.

The luciferase assay of both transient and stably transfected cells was performed in the same manner. After induction of cells with androgens or antiandrogens for 48 hours, media was removed and 50 µL of lysis reagent added (0.1M potassium phosphate buffer at pH 7.8, 1% triton X-100, 1 mM dithiothreitol, 2 mM EDTA) to each well. Cells were assayed within 15 minutes of lysis or stored at −80° C. until analysis. Storage of cell lysates at −80° C. for five days or less did not result in significant loss of luciferase activity.

The Enhanced Luciferase Assay Kit (Analytical Luminescence Laboratory, MI) was used to quantitate the extent of luciferase activity from PSE-Luc transfected LNCaP cells. A Dynatech 3000 96-well plate luminometer (Dynatech, VA) was used to measure the amount of light generated from the assay. The instrument was run in the Enhanced Flash Mode, employing a dual injector system for substrate addition. Optimal assay conditions and Luminometer parameters were as follows: addition of 60 µL of Substrate A (buffer), 1 second delay, addition of 60 µL of Substrate B (luciferin reagent), 1 second delay, integrate signal for 3 seconds. The results are depicted as the integral sum in relative light units (RLUs). The extent of induction by androgens/antiandrogens, e.g. fold induction, was determined by: fold induction=RLUs [x nM drug]/RLUs [0 nM drug].

CMV-Luc/LNCaP Cell Line. Transfections of the control plasmid, CMV-Luc, into LNCaP cells were done in the same fashion as for PSE-Luc. The stable cell line CN1006, containing CMV-Luc, was obtained by selection with G418. The luciferase assay was performed as described above.

Results

Transient Transfections of LNCaP Cells with PSE-Luc. The effectiveness of utilizing PSE-Luc in transient transfections as a transcription screening assay for agonist/antagonist type molecules was examined in LNCaP cells. This transcription assay was evaluated for its use in a 96-well format. The androgens, methyl trienolone (R1881) and dihydrotestosterone (DHT), were used to induce different degrees of luciferase expression under the control of the prostate-specific enhancer.

The inducibility of PSE-Luc by the synthetic androgen R1881 in transiently transfected LNCaP cells was determined. Cells were plated into an opaque 96-well plate at a cell density of $4 \times 10^4$ cells/well per 100 µL, followed by 50 µL of a 3× media solution containing either R1881 or DHT. Cells were incubated for 48 hours, lysed and assayed for luciferase expression. The extent of induction was determined by dividing the amount of luciferase expression (RLUs) at X nM hormone by the amount of expression without hormone. At 0 nM R1881, luciferase expression in transfected LNCaP cells was similar to background levels (approximately 1–5 RLUs). The addition of 1–50 nM R1881 resulted in an approximately 275 fold induction of luciferase expression (3,000–3,500 RLUs) over uninduced transfected cells. Peak levels of luciferase expression were obtained at 1 nM R1881, which closely corresponds to physiological levels of androgen. Variations in the amount of DNA/Lipid complexes used in transient transfections resulted in comparable results, however lower DNA concentrations (e.g. 1 and 2 µg DNA) gave smaller RLU values after induction. Lastly, %CV varied ranging from 10–30%.

A second androgen, dihydrotestosterone (DHT), was evaluated for its inducibility of transiently transfected LNCaP cells. DHT is a naturally occurring human androgen and the reductive analog of testosterone. The extent of fold induction increased with increasing concentration of DHT. Peak levels of approximately 100 fold were obtained over the background value of 25 RLUs for DHT concentrations of 100 and 200 nM (e.g. 2,500–3,000 RLUs). A comparison of R1881 and DHT shows that approximately 100 fold more DHT is required relative to R1881 to obtain comparable luciferase activity. The difference in fold induction between the two androgens, e.g. 100 vs. 250 fold induction, can be explained by a 2 fold higher background signal for the DHT (12 vs. 25 RLUs), which likely resulted from the particular experimental procedures employed. However, the overall peak expression levels stimulated by the two androgens are comparable. The higher concentration of DHT required to achieve the same luciferase expression levels obtained with R1881 is addressed later.

Androgen and Antiandrogen Responsiveness of Stably Transfected PSE-Luc/LNCaP Cell Line. LNCAP cells were co-transfected with PSE-Luc and pcDNA3 containing the neomycin gene. LNCaP clones containing both genes were selected with G418 and examined for luciferase expression after induction with either androgen or antiandrogens. As in the case of transient transfections with PSE-Luc, the assay is evaluated in the 96-well format for high throughput screening (HTS) of potential agonist/antagonist.

The hormones R1881 and DHT were utilized to screen for androgen-responsive LNCaP clones containing the PSE-Luc genes. Two clones, designated CN1010 and CN1013, exhibited luciferase activity upon incubation in 1 nM R1881 and were characterized further with varying concentrations of R1881 and DHT. The androgen-responsiveness profile of CN1013 is similar to that obtained for transient transfections. Peak values of R1881 induction were obtained at physiological levels (0.1–1 nM), while DHT required 100–200 fold greater amounts for comparable expression. The $EC_{50}$ of R1881 in CN1013 was 0.075 nM.

Figure 1B:
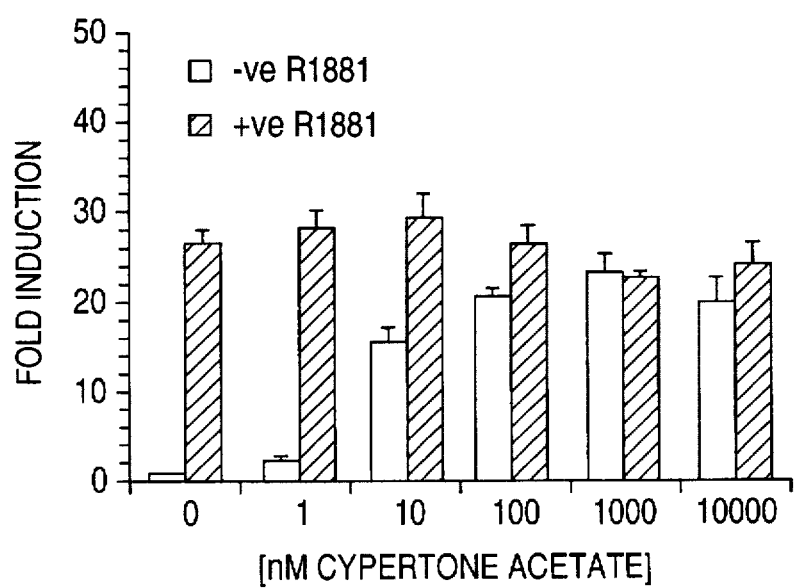

The luciferase responsiveness of CN1013 to antiandrogens, hydroxy-flutamide (HO—Flu) and cyproterone acetate (Cypro. A), as well as their antagonist behavior to R1881 (1 nM) induced cells was evaluated. Incubation of CN1013 with either antiandrogen resulted in luciferase expression levels similar to that obtained for R1881, but only at elevated concentrations of 100–1,000 fold higher (FIGS. 1A and 1B); zero or minimal expression was observed at physiological concentrations. The antiandrogens ability to inhibit luciferase expression after induction with 1 nM R1881 is also shown in FIG. 1. At all antiandrogen concentrations examined, there was neither inhibition nor induction of luciferase expression after R1881 had been added. The addition of other non-steroidal intracellular receptor ligands unrelated to the androgen receptor, i.e. retinoic acid (RA), did not result in either induction or inhibition of CN1013.

The intra-assay %CVs of the stable cell line CN1013 typically varied between 5–10%. While the initial characterization of CN1013 resulted in %CV slightly higher than 10%, later experiments were able to lower the intra-assay %CV to an acceptable range (FIGS. 1A and 1B). Transient transfection assays yielded %CVs of 10–30%, whereas stable cell line assays (CN1013), yielded %CVs of 5–10%.

Metabolism of Dihydrotestosterone (DHT) in CN1013 Cell Line. The higher levels of DHT needed to induce luciferase expression in either CN1013 or transient transfections was investigated. The decrease of DHT concentration in CN1013 cells was measured kinetically utilizing the Testosterone ELISA Kit by Neogen Corporation (100% cross reactivity with DHT). The metabolism of DHT occurs rapidly within 1–4 hours of addition to CN1013 cells, while the DHT concentration remained constant when unexposed to CN1013 cells. The half life of 10 nM DHT in CN1013 cells was calculated to be approximately 1.1 hours. The metabolized product was not identified.

While the overall luciferase expression levels between transient transfections and CN1013 are similar (3000–4000 RLUs), the extent of fold induction upon androgen addition is approximately 5–10 times lower in the latter case due to significant background signal (e.g. 100–200 RLUs). The larger background signal is a result of the requirement of growing CN1013 in hormone containing RPMI. Incubation of CN1013 in 10% strip-serum RPMI (minus hormone) prior to plating into 96-well plates lowered background signal moderately. Further decreases in overall luciferase expression were observed with passage number of the cell line. A comparison of the RLUs at passage 5 and 15 showed an approximate 3–5 fold decrease in luciferase expression, however the overall level of induction remained identical.

The decrease in luciferase expression of CN1013 with increasing passage number resulted in the need to select subclones having enhanced expression levels. Subclones of PSE-Luc/LNCaP were obtained from the parental cell line CN1013 by limiting dilution. Screening of these clones produced a single active clone, designated CN1013.7, which was 5–10 times more active than the parental cell line yielding 100–200 fold induction with R1881.

Luciferase Expression of CMV-Luc/LNCaP Stable Cell Line. LNCaP clones containing the CMV-Luc gene were screened for stable expression of the luciferase gene (i.e. selection of stable cell line). A 3–4 fold increase in expression levels over the uninduced cells was observed upon the addition of 10–1000 nM androgen. A similar androgen stimulation of CMV-Luc expression in transient transfection of LNCaP cells was reported by Pang et al., Hum. Gene Ther. (1995) 6:1417–1426. The slight increase in expression levels was attributed to cell proliferation resulting from increased R1881 addition.

It is evident from the above results that a simple and rapid screening method is provided for determining activity of compounds in inhibiting proliferation of prostate cancer. The method employs cells which are stable, can be easily grown, and can be used in a conventional format to identify the activity of specific compounds. The results are at least semi-quantitative, and allow for high throughput screening with automated equipment.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for screening drugs for the treatment of prostate cancer employing prostate cells containing an endogenous androgen receptor and an expression construct, wherein the expression construct comprises a transcriptional initiation region of a prostate specific enhancer from a prostate specific antigen (PSA) gene and a promoter and a gene whose expression product provides a detectable signal, wherein said gene is under the transcriptional control of said transcriptional initiation region, the method comprising:

combining said cells with a candidate drug in the presence of an androgen for sufficient time for detectable expression of said gene; and detecting the level of expression of said gene as compared to the level of expression in the absence of said candidate drug.

2. A method according to claim 1, wherein said gene expresses an enzyme.

3. A method according to claim 2, wherein said enzyme is luciferase.

4. A method according to claim 3, wherein said detecting comprises:

lysing said prostate cells; and assaying said lysate for luminescence.

5. A method according to claim 1, wherein said androgen is methyl trienolone or dihydrotestosterone.

6. A method for screnig drugs for the treatment of prostate cancer employing prostate cells containing an endogenous androgen receptor comprising an expression construct which comprises a transcriptional initiation region of the prostate specific antigen enhancer and a promoter and a gene encoding an enzyme which catalyzes a reaction resulting, in a detectable signal, wherein said gene is under the transcriptional control of said transcriptional initiation region, said method comprising:

combining said prostate cells with a candidate drug in the presence of methyl trienolone or dihydrotestosterone for sufficient time for detectable expression of said enzyme;

lysing said prostate cells to provide a lysate and adding the substrate of said enzyme to said lysate; and detecting the level of expression of said enzyme as compared to the level of expression in the absence of said candidate drug.

7. A method according to claim 6, wherein said prostate cells are LNCAP cells and said enzyme is luciferase.

8. The method according to claim 1, wherein the prostate specific antigen enhancer comprises a sequence encompassing nucleotides between about −5824 to about −3738 of the upstream region of the PSA gene, said enhancer no more than about 5.8 kb in length and wherein the enhancer exhibits enhancer activity.

9. The method according to claim 1, wherein the prostate specific enhancer is contained within a polynucleotide fragment of about 5.8 kilobases from about −5824 to about +1 of the upstream region of the PSA gene, wherein the enhancer exhibits enhancer activity.

10. The method according to claim 8, wherein the promoter comprises a sequence encompassing nucleotides between about −560 to about +7 of the PSA gene.

11. A method according to claim 6, wherein the prostate specific antigen enhancer comprises a sequence encompassing nucleotides between about −5824 to about −3738 of the upstream region of the PSA gene, said enhancer no more than about 5.8 kb in length and wherein the enhancer exhibitis enhancer activity.

12. The method according to claim 6, wherein the prostate specific enhancer is contained within a polynucleotide fragment of about 5.8 kilobases from about −5824 to about +1 of the upstream region of the PSA gene, wherein the enhancer exhibits enhancer activity.

13. The method according to claim 11, wherein the promoter comprises a sequence encompassing nucleotides between about −560 to about +7 of the PSA gene.

* * * * *